United States Patent
Hsieh

(10) Patent No.: US 12,000,970 B2
(45) Date of Patent: Jun. 4, 2024

(54) SYSTEM AND METHOD FOR CHARGE SHARING COMPENSATION FOR X-RAY PHOTON COUNTING DETECTORS

(71) Applicant: The Regents of the University of California, Oakland, CA (US)

(72) Inventor: Scott S. Hsieh, Anaheim, CA (US)

(73) Assignee: The Regents of the University of California, Oakland, CA (US)

( * ) Notice: Subject to any disclaimer, the term of this patent is extended or adjusted under 35 U.S.C. 154(b) by 227 days.

(21) Appl. No.: 17/602,962

(22) PCT Filed: May 1, 2020

(86) PCT No.: PCT/US2020/030966
§ 371 (c)(1),
(2) Date: Oct. 11, 2021

(87) PCT Pub. No.: WO2020/223605
PCT Pub. Date: Nov. 5, 2020

(65) Prior Publication Data
US 2022/0187478 A1  Jun. 16, 2022

Related U.S. Application Data

(60) Provisional application No. 62/841,466, filed on May 1, 2019.

(51) Int. Cl.
*G01T 1/17* (2006.01)
*A61B 6/00* (2006.01)
*A61B 6/42* (2024.01)

(52) U.S. Cl.
CPC ............ *G01T 1/171* (2013.01); *A61B 6/4241* (2013.01)

(58) Field of Classification Search
CPC ............ G06T 2211/00; G06T 2211/40; G06T 2211/408; G06T 11/005; G01T 1/36;
(Continued)

(56) References Cited

U.S. PATENT DOCUMENTS 7,617,270 B2 * 11/2009 Nikitin ............... G06G 7/02
708/801
9,031,197 B2  5/2015 Spahn
(Continued)

OTHER PUBLICATIONS

Lundqvist, Silicon Strip Detectors for Scanned Multi-Slit X-Ray Imaging, Kungl Tekniska Hogskolan, Fysiska Institutionen, Stockholm, 2003, 169 pages.
(Continued)

*Primary Examiner* — John R Lee
(74) *Attorney, Agent, or Firm* — Quarles & Brady LLP

(57) ABSTRACT

A system for charge sharing compensation for a photon counting detector. A plurality of comparators, each configured to generate comparator output data based on a threshold value, a plurality of energy bins, each of the plurality of energy bins coupled to one of the plurality of comparators, and a coincidence logic coupled to two or more of the plurality of comparators and configured to receive comparator output data associated with two or more of a plurality of pixels. The comparator output data for each pixel indicates when a signal associated with the pixel crosses a threshold value. The coincidence logic is configured to generate a coincidence output when the comparator output data for a first pixel is received within a predetermined time interval of the comparator output data for a second pixel. The system includes a coincidence counting bin coupled to the coincidence logic and configured to receive the coincidence output and generate count data based on the coincidence output.

14 Claims, 10 Drawing Sheets

(58) Field of Classification Search
CPC ......... G01T 1/1663; G01T 1/172; G01T 1/17; G01T 1/171; A61B 6/42; A61B 6/4208; A61B 6/4241

See application file for complete search history.

(56) References Cited

U.S. PATENT DOCUMENTS

| | | | |
|---|---|---|---|
| 9,599,730 B2 | 3/2017 | Spahn | |
| 10,292,669 B2* | 5/2019 | Ishitsu | A61B 6/4258 |
| 11,540,791 B2* | 1/2023 | Goederer | A61B 6/5205 |
| 11,675,096 B2* | 6/2023 | Goederer | G01T 1/247 |
| | | | 250/370.08 |
| 2009/0259709 A1* | 10/2009 | Nikitin | G06G 7/02 |
| | | | 708/801 |
| 2012/0112088 A1* | 5/2012 | Abraham | G01T 1/171 |
| | | | 250/336.1 |
| 2019/0025440 A1 | 1/2019 | Steadman Booker et al. | |
| 2021/0186440 A1* | 6/2021 | Kreisler | A61B 6/032 |
| 2021/0190979 A1* | 6/2021 | Goederer | G01T 1/247 |
| 2022/0187478 A1* | 6/2022 | Hsieh | A61B 6/4241 |
| 2023/0136957 A1* | 5/2023 | Göederer | A61B 6/4241 |
| | | | 378/19 |

OTHER PUBLICATIONS

European Patent Office, Extended Search Report, Application No. 20799469.0, dated Jan. 3, 2023, 9 pages.

Blevis et al., Spectroscopy in Computed Tomography Using Pixelated Photon Counting Detectors, Workshop on Medical Applications of Spectroscopic X-ray Detectors, 2015, 2 pages.

Hsieh, Coincidence Counters for Charge Sharing Compensation in Spectroscopic Photon Counting Detectors, IEEE Transactions on Medical Imaging, 2020, 39(3):678-687.

Stierstorfer, Modeling the Frequency-Dependent Detective Quantum Efficiency of Photon Counting X-ray Detectors, Medical Physics, 2018, 45(1):156-166.

PCT International Search Report and Written Opinion, PCT/US2020/030966, dated Aug. 18, 2020, 9 pages.

* cited by examiner

SYSTEM AND METHOD FOR CHARGE SHARING COMPENSATION FOR X-RAY PHOTON COUNTING DETECTORS

CROSS-REFERENCE TO RELATED APPLICATION

This application represents the national stage entry of International Application No. PCT/US2020/030966, filed May 1, 2020 which claims the benefit of and priority to U.S. Ser. No. 62/841,466 filed May 1, 2019 and entitled "System And Method For Charge Sharing Compensation For X-Ray Photon Counting Detectors", which is incorporated herein by reference in its entirety.

BACKGROUND

Energy discriminating, photon counting detectors (PCDs) for CT applications have undergone rapid development in recent years. PCDs offer several distinct advantages when compared to the conventional energy-integrating detectors currently used in CT systems. PCDs estimate the energies of individual photons arriving at the detector. PCDs operate by comparing a signal to multiple fixed thresholds via comparators. This allows them to classify the energy of each photon arriving at the detector. When equipped with three or more energy bins, PCDs can provide multi-material imaging with two different contrast agents. PCDs can also provide retrospective spectroscopic imaging without a specific dual-energy protocol that would restrict the choice of kVp. PCDs may offer spatial resolution far superior to conventional detectors. By adjusting the weights applied to each energy bin to emphasize low energy photons, PCDs can enhance iodine contrast signal and improve iodine detectability. Finally, PCDs do not have electronic noise in the traditional sense and may offer greater dose efficiency for low dose scans where electronic noise reduces detectability.

Multiple PCD systems have been developed. For example, a scanner has been developed that is able to operate at the high flux regime with little observable penalty, at least for non-spectral tasks. A PCD prototype was integrated into a diagnostic scanner and has reported results in phantom studies. Another example has led to a very fast (~100 ns deadtime) PCD with a small pixel pitch of 0.1 mm. Another PCD has been developed that has several advanced features, including a charge summing mode. Compared to early work in PCDs, these newer prototypes are capable of much greater count rate capability and have overcome many challenges.

In the early days of PCD development, it was sometimes thought that PCDs could provide large benefits for spectral tasks. Ideal PCDs that correctly infer the energy of every incident photon can outperform conventional dual-energy approaches. However, it must be understood that while real PCDs have a variety of useful properties, real PCDs also have several non-idealities and limitations such as, for example, pulse pileup and charge sharing. When photons arrive too quickly onto the detector, their pulses merge or "pile up" and counts are lost. PCDs are typically modeled with an inactive dead time that follows each incident photon. The inverse of the dead time, the characteristic count rate, is also used to describe PCDs. When the incident flux arriving at the detector is ~20% of the characteristic count rate, the spectral advantages of an otherwise ideal PCD are lost. The performance of X-ray PCDs, especially on spectral tasks, may also be compromised by charge sharing. Charge sharing is when a single photon deposits charge into multiple pixels and appears as two independent low-energy events in close spatiotemporal proximity.

Current PCD designs for CT applications must handle the intense count rates that are characteristic of diagnostic scanners, which can exceed $10^9$ counts per second per square millimeter. To accommodate these high flux levels, PCDs are often designed with small pixel sizes to increase the characteristic count rate per unit area. To reduce pileup, some PCDs have reduced pixel size to increase the characteristic count rate per unit area. However, reducing pixel size increases the prevalence of charge sharing.

Several approaches have been proposed for charge sharing compensation. For example, charge summing circuitry has also been proposed to combat the effects of charge sharing. Charge summing circuitry has been implemented using analog summation and arbitration circuits. Analog charge summing (ACS) is a very powerful tool for restoring corrupted photons. Charge summing circuits increase the effective dead time of the detector by factors ranging from 4 to 9 depending on implementation details because photons that randomly arrive in close spatiotemporal proximity can mimic the appearance of a charge sharing event and would be inadvertently summed together. Analog charge summing (ACS) requires modifications to analog circuitry that are nontrivial to implement. In addition, analog charge summing reduces count rate capability which is essential in CT. An alternative to analog charge summing is "digital count summing" (DCS). DCS is a type of anti-coincidence logic performed in the digital domain that recognizes coincident events in neighboring pixels. These events are then combined into a single count of higher energy. DCS operates after the comparator digitization and may offer implementation advantages over ACS. Like ACS, DCS increases the effective dead time of the PCD and is disadvantageous in high flux scenarios. In addition, DCS reduces count rate capability. Existing mechanisms for charge sharing compensation such as charge summing and larger pixel sizes also increase pileup which is undesirable.

Several prior approaches have tried to mitigate charge sharing without sacrificing count rate capability. The tradeoff between these two factors is mediated strongly by pixel pitch. Several prior strategies have been disclosed that attempt to combine the benefits of both small and large pixels. One disclosed approach is to route the energy signals from a PCD pixel through a flexible network that can dynamically couple pixels together into larger groups so that the benefits of a larger pixel size can be used when the flux is appropriately low. A similar approach is to split the analog charge signal into a small pixel pathway and a joint macropixel pathway and process these two in parallel, combining their data later with a crossfading weight. Other methods that have been described include selective switching between a high-flux mode and a high energy-resolution mode wherein the high energy-resolution mode includes anticoincidence logic similar to DCS, or parallel processing of a single larger PCD pixel with slow and fast pulse shaping circuits, the latter of which could prevent paralysis at high flux. Many of these concepts require modifications in the analog circuitry or the design of new components.

SUMMARY OF THE DISCLOSURE

In accordance with an embodiment, a system for charge sharing compensation for a photon counting detector includes a plurality of comparators, each of the plurality of comparators configured to generate comparator output data based on a threshold value, a plurality of energy bins, each of the plurality of energy bins coupled to one of the plurality of comparators, and a coincidence logic coupled to two or more of the plurality of comparators and configured to receive comparator output data associated with two or more of a plurality of pixels. The comparator output data for each pixel indicates when a signal associated with the pixel crosses a threshold value. The coincidence logic is configured to generate a coincidence output when the comparator output data for a first pixel is received within a predetermined time interval of the comparator output data for a second pixel. The system further includes a coincidence counting bin coupled to the coincidence logic and configured to receive the coincidence output and generate count data based on the coincidence output.

In accordance with another embodiment, a method for charge sharing compensation for a photon counting detector includes providing comparator output data associated with each of a plurality of pixels from a plurality of comparators to a coincidence logic and a plurality of energy bins. The comparator output data for each pixel indicates when a signal associated with the pixel crosses a threshold value. The method further includes generating, using the coincidence logic, a coincidence output when the comparator output data for a first pixel is received within a predetermined time interval of the comparator output data for a second pixel, generating count data based on the coincidence output using a coincidence counting bin, generating an image based on the count data and data from each of a plurality of energy bins, and displaying the image.

BRIEF DESCRIPTION OF THE DRAWINGS

The present invention will hereafter be described with reference to the accompanying drawings, wherein like reference numerals denote like elements.

DETAILED DESCRIPTION

Figure 1:
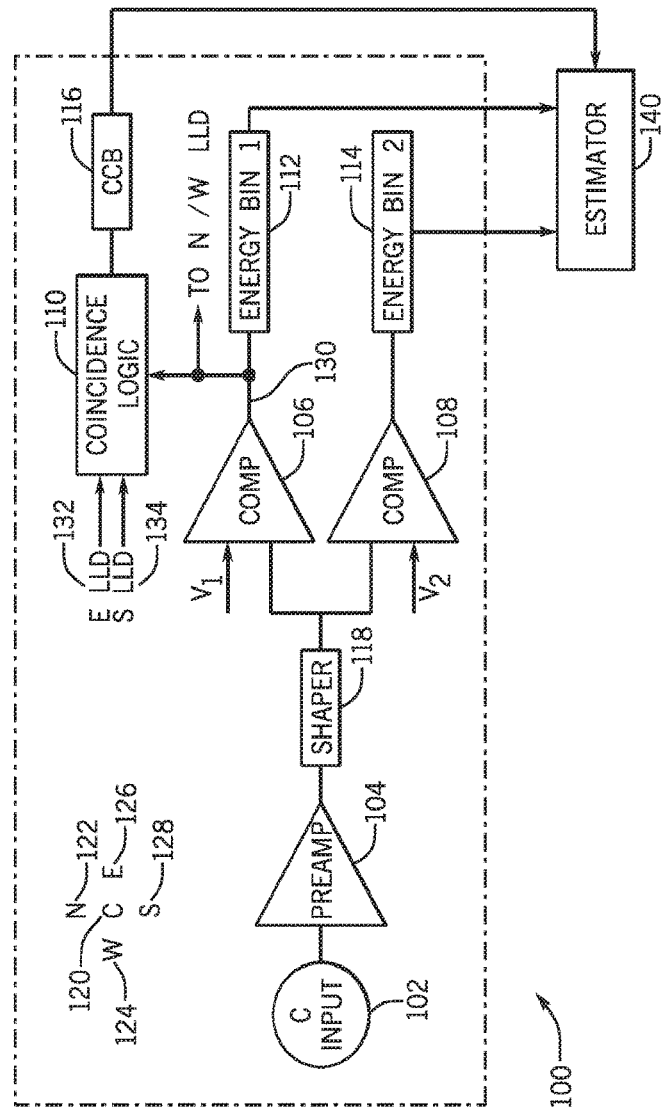
FIG. 1 is a circuit diagram of a photon counting detector (PCD) and coincidence counting bin (CCB) in accordance with an embodiment.

The present disclosure describes a system and method for charge sharing compensation for photon counting detectors (PCDs). In particular, the present disclosure describes a coincidence counting bin (CCB) that is used to provide charge sharing compensation. The CCB is a coincidence counter that is configured to count charge sharing events, inferred by coincidence in neighboring pixels. FIG. 1 is a circuit diagram of a photon counting detector (PCD) with a coincidence counting bin (CCB) in accordance with an embodiment. Photon counting detector 100 includes comparators 106, 108 and counters 112, 114 which are energy bins (e.g., a first energy bin 112 and a second energy bin 114). In FIG. 1, two energy bins 112, 114 are shown, however, in other embodiments, more than two energy bins may be present in the detector. In an embodiment, the first energy bin 112 has a lower energy threshold the second energy bin 114. A signal, e.g., pixel input 102, is pre-amplified using a preamplifier 104 and pulse shaped sing a pulse shaper 118 and then passed through the comparators 106, 108. In an embodiment, the pixel input 102 is a signal from a center pixel, labeled as C 120. Comparators 106, 108, compare the pixel input 102 to multiple fixed thresholds. Based on the comparison, each comparator 106, 108 classifies the energy of each photon arriving at the detector 100. A counter (or energy bin) 112, 114 is incremented each time a voltage signal crosses (e.g. up-crossing) the threshold of a corresponding comparator 106, 108. For example, energy bin 112 is incremented when a voltage signal crosses the threshold value of comparator 106 and energy bin 114 is incremented when a voltage signal crosses the threshold value of comparator 108. When photons deposit charge across multiple pixels, however, the classification of the signal will be in error, and often a single high energy photon will be misread as two low energy photons (i.e., charge sharing).

Coincidence logic 110 and a coincidence counter or coincidence counting bin (CCB) 116 are configured to receive an output 130 (e.g., a digital output) of the comparator (e.g., comparator 106) at the lowest energy level, also called the lowest level discriminator (LLD) so that the LLD output 130 may be used for coincidence detection. The LLD output is also provided to the associated counter for the first energy bin 112. Coincidence logic 110 also receives LLD output data for a plurality of adjacent pixels (e.g., two or more of the "N" 122, "W" 124, "E" 126, and "S" 128 pixels shown in FIG. 1). The coincidence logic 110 and the CCB 116 use the LLD output for coincidence detection. The CCB 116 is triggered by coincident events in neighboring pixels and provides an estimate of the double counts arising from charge sharing. Accordingly, the CCB 116 is incremented each time a coincidence is detected by coincidence logic 110 between two adjacent pixels. For example, if the LLD (or lowest energy bin) 130 of one pixel (e.g., the center pixel "C" 120) is triggered within a short time interval or window (e.g., the characteristic width of the pulse shaping circuitry 118) of either the LLD (or lowest energy bin) 132 for the right ("E") pixel or the LLD 134 of the bottom ("S") pixel (as shown in FIG. 1), the coincidence logic 110 activates and increments the counter for the CCB 116. In an embodiment, to increment the CCB 116 adjacent pixels may be required to be triggered within the standard deviation of the pulse shaping function of, for example the pulse shaper 118. The pulse shaping function is controlled by the underlying hardware but could be modeled, for example, as a Gaussian with standard deviation $\sigma=40$ ns. In this example, the total interval for which the coincidence logic 110 waits for a count in an adjacent pixel would therefore be $2\sigma=80$ ns.

In the low flux limit, coincidences arise only from charge sharing, but as flux increases, coincidences can occur because of two protons which independently arrive in close spatiotemporal proximity. As mentioned, the energy bins 112, 114 are incremented each time the voltage signal from the input 102 crosses a comparator 106, 108 threshold. In contrast, CCB 116 measures the aggregate level of charge sharing, specifically, the number of double counts. Accordingly, the CCB 116 identifies simultaneous detection of adjacent pixels. The CCB 116 may be read out similar to an energy bin 112, 114 and the count information from the CCB 116 may be provided to an estimator 140. The outputs of the first energy bin 112 and the second energy bin 114 are also provided to the estimator 140. The estimator 140 is used to convert the raw bin data from the CCB 116 and the energy bins 112, 114 to spectral images. For example, the estimator 140 may be used to determine spectral estimates as described further below. The count information from CCB 116 may, for example, be used by the estimator 140 to improve the noise (and quality) of spectral estimates generated by the estimator 140.

While many known types of charge sharing compensation (e.g., charge summing) attempt to restore or correct the charge sharing events (e.g., restore the energy of individual photons that have been corrupted by charge sharing), the coincidence logic 110 and CCB 116 do not directly restore corrupted events. Rather, the CCB 116 measures the aggregate level of charge sharing, specifically, the number of double counts. Because the CCB 116 does not modify the signal processing pathway of existing energy bins (e.g., energy bins 112, 114), the CCB 116 does not reduce the count rate capability of the PCD 100. The coincidence logic 110 and CCB 116 may be implemented using simple digital logic after the comparator. The CCB does not increase pile up and may be implemented in a similar fashion to existing energy bins in the PCD. From the standpoint of implementation complexity, integrating the CCB may be comparable to or simpler than adding a new energy bin. In an embodiment, the CCB may be realized by simply replacing a comparator with digital coincidence logic, which converts a regular energy bin into the CCB. Another advantage of using a CCB 116 for charge sharing compensation is that it does not damage high flux performance because it does not alter existing comparators and counters. Most charge summing circuits, when active, will be harmful at high flux. The CCB will count random, unconnected coincidences at high flux, but its output can be simply discarded.

In an embodiment, a separate CCB may additionally be used to track coincidences in a different pair of energy bins, such as the coincidence of two energy bins at increased energy. In various simulations which are described further below, it was observed that the most valuable coincidences to track are those from the LLD, assuming the LLD is in the range of 20 to 30 keV. In the examples described herein, it is assumed that only one CCB is used and that it is tied to the LLD output. Reducing the LLD, or tying the CCB to an energy bin that is below the LLD, may improve its performance. In an embodiment, a more complex form of the CCB may include coincidence logic that is able to differentiate random coincidences from that of charge sharing. For example, if a coincidence is detected at two high energy bins, it could be deduced that the coincidence cannot be from a single photon. In an example, if the maximum photon energy is 140 keV and a coincidence is detected at the 80 keV bin, it may be inferred that these two events originate from two separate photons. A multi-step coincidence counter may integrate the coincident events at different energies to determine whether or not the CCB should be incremented.

In an embodiment where the PCD includes two energy bins, the CCB 116 may be viewed as equivalent to charge summing. If low-energy photons are always detected in the low energy bin, but high energy photons are either correctly detected or incorrectly detected as two low energy photons in adjacent photons due to charge sharing, the CCB 116 can be interpreted to mean that the low energy bin has been overcounted and the high energy bin has been undercounted. In an embodiment where more than two energy bins are used, it may be difficult to provide a physical interpretation for the CCB. In particular, it is not apparent how knowledge of the CCB can approximate charge summing circuitry. With multiple energy bins, the CCB only describes the cumulative number of double counts and does not record the energies of the photons that were affected. A separate physical explanation of the CCB stems from noise correlations. When charge sharing occurs, pixels experience noise correlations: a single photon can increment multiple adjacent low energy bins. Some of these counts will be erroneous. Furthermore, the counts in the CCB will be highly correlated with the erroneous excess counts that arise from charge sharing. An estimator algorithm can then use the CCB counts as a correction, knowing that the number of counts in the CCB is correlated with the error in the conventional energy bins measurement.

Figure 2:
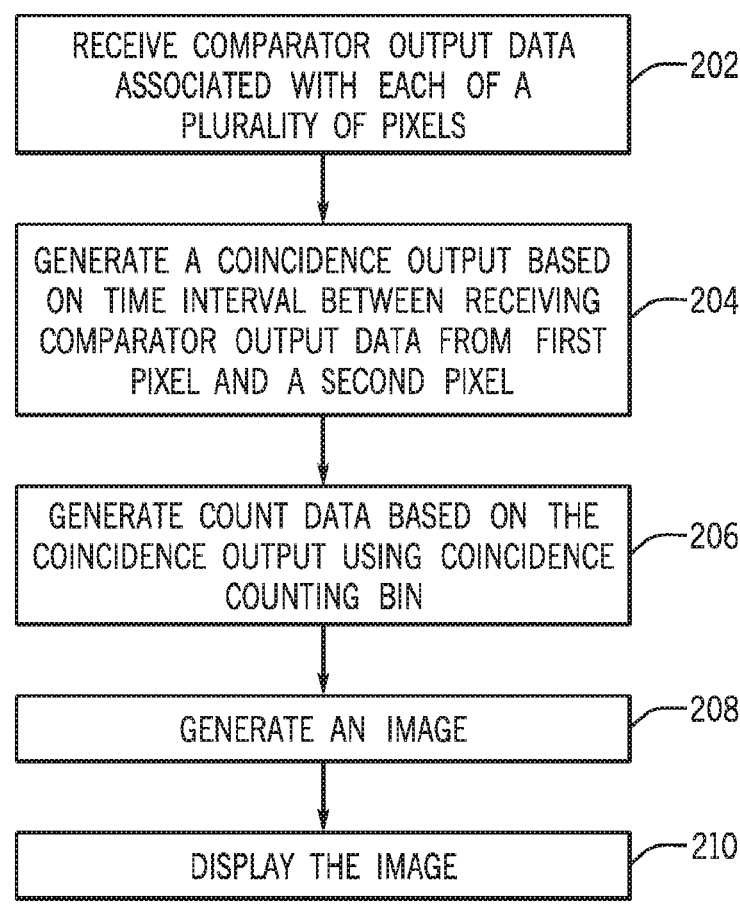
FIG. 2 illustrates a method for charge sharing compensation in accordance with an embodiment.

FIG. 2 illustrates a method for charge sharing compensation in accordance with an embodiment. At block 202, comparator output data associated with each of a plurality of pixels is received by, for example, coincidence logic 110 (shown in FIG. 1) from a plurality of comparators. In an embodiment, the comparators are included in a PCD and the comparator output data for each pixel indicates when a signal associated with the pixel crosses a threshold value. The comparator output data may also be provided to a counter that is associated with an energy bin (e.g., energy bin 112 or 114 shown in FIG. 1) that may be incremented each time the signal associated with the pixel crosses the threshold value. At block 204, a coincidence output is generated using the coincidence logic when the comparator output data for a first pixel is received by the coincidence logic within a predetermined time interval of the comparator output data for a second pixel. At block 206, count data is generated based on the coincidence output using a coincidence counting bin (CCB) (e.g., CCB 116 shown in FIG.1) which is coupled to the coincidence logic. The CCB count data is incremented each time a coincidence is detected between two adjacent pixels. By counting each time a coincidence is detected between two adjacent pixels, the aggregate level of charge sharing is measured, specifically, the number of double counts. At block 208, an image may be generated based on the count data and data from each of the plurality of energy bins. In one embodiment, an image may be generated using an estimator (e.g., estimator 140 shown in FIG. 1). Knowledge of the number of coincident counts may be used (e.g., by an estimator) to reduce noise. At block 210, the image may be displayed on a display, for example, of a computer system as described below with respect to FIG. 10.

The following examples set forth, in detail, ways in which the present disclosure was evaluated and ways in which the present disclosure may be used or implemented and will enable one of ordinary skill in the art to more readily understand the principles thereof. The following examples are presented by way of illustration and are note meant to be limiting in any way.

The focus of the examples described herein is primarily on the spectral applications of PCDs. In particular, the examples and simulations involve PCDs that use cadmium telluride (CdTe) as a substrate. It should be understood that materials such as silicon may be used. In addition, the examples use PCDs that use a bank of comparators and counters for energy discrimination. In various examples discussed herein, a PCD was simulated with and without the CCB using Monte Carlo simulations, modeling PCD pixels as instantaneous charge collectors and x-ray energy deposition as producing a Gaussian charge cloud with 75 micron FWHM. With typical operating conditions and at low flux (120 kVp, incident count rate 1% of characteristic count rate, 30 cm object thickness, 5 energy bins, pixel pitch of 300 microns), the CCB improved dose efficiency of iodine and water basis material decomposition by 70% and 50%, respectively. An improvement of 20% was also seen in an iodine CNR task. These improvements are attenuated as incident flux increases and show moderate dependence on filtration and pixel size. It was also shown that the radiation dose efficiency improvement of using the coincidence counting bin (CCB) can be up to 80% for spectroscopic tasks, which is much larger than what might be expected. At low flux, and for pixel size of 200-400 microns, spectral performance may be improved by 50-80%.

In various examples described herein, the bombardment of photons passing through an object of known thickness onto a CdTe substrate in a PCD was simulated using a known simulation tool for the simulation of the passage of particles through matter. The location and quantity of energy deposition was tracked. A known computing environment for mathematical analysis and simulation was used to simulate approximate charge transport in the pixel, assuming the pixels are perfect collectors and that the charge cloud is a Gaussian with FWHM of 75 microns. The energy deposition events were transformed into charge clouds with the charge distributed according to a 3D Gaussian distribution and with a ratio of one charge to every 10 eV of deposited energy. In this example, the standard deviation of the Gaussian distribution was fixed at 32 microns independent of energy. If a larger charge cloud is assumed, charge sharing increases and hence the benefit of any charge sharing compensation mechanism also increases. To model pileup, the deposition of photons onto the substrate may be simulated with a time digitization of 10 ns. The characteristic count rate at the detector was 7 Meps/pixel. To combine the different bins (energy or CCB) in an optimal fashion, a convex optimization may be used to determine the optimal linear estimator. The true estimator is not linear but images were restricted to low contrast perturbations about a background operating point so that the estimator could be approximated using a first-order linear expansion. Energy thresholds were 25/65 keV for the 2-bin case and 25/45/65/85/105 for the 5-bin case. Tube potential was 120 kVp in all simulations.

Table 1 compares the size of the charge cloud used for simulations with the PCD and CCB system (shown in FIG. 1) with two other known models that have been fitted to experimental data. The two known models used for comparison are (1) Blevis I, Daerr H, Rokni M, Hermann C, Istel T, Livne A, Martens G, Peyrin F, Rubin D, Sigovan M, Steadman R, Thran A, Brendel B, Levinson R, Altman A, Zarchin O, Boussel L, Douek P, Roessl E. In: Spectroscopy in computed tomography using pixelated photon counting detectors; Workshop on medical applications of spectroscopic X-ray detectors; Geneva, Switzerland; 2015 and (2) Stierstorfer K. Modeling the frequency-dependent detective quantum efficiency of photon-counting x-ray detectors. Med Phys. 2018; 45(1): 156-166. In the work of Blevis, the spherical charge cloud had an energy-dependent radius with different values reported at 60 and 120 keV. The size of the charge cloud for the examples and simulations herein was chosen to be intermediate between these two models. All charges are instantaneously collected if they fall within the boundaries of the pixel. This is a simplification of the Coulomb repulsion and diffusion processes that occur as the charges drift through the detector. More accurate results may be obtained if the charge cloud size were to vary according to depth of interaction, or by simulation of the current induced by the charge cloud motion. However, a simple charge cloud model with the perfect collection approximation was chosen for simplicity.

TABLE 1

| Reference | Model | Param | FWHM | FWTM |
| --- | --- | --- | --- | --- |
| Blevis | Sphere | R = 50-75 um | 100-150 um | 100-150 um |
| Stierstorfer | Gaussian | SD = 21 um | 50 um | 90 um |
| Present Disclosure | Gaussian | SD - 32 um | 75 um | 135 um |

In the examples herein, the charge is summed within the boundaries of each pixel in a 5 by 5 neighborhood of pixels centered on the incident photon. This allows the emission and absorption of characteristic photons up to two pixels away to be tracked, but scatter to greater distances is neglected. A library of these interactions was precomputed at 5 keV energy intervals between 30 and 120 keV, and 20,000 precomputed entries were simulated at each energy level. By simply summing within the square boundaries of the pixel, the example simulations neglect the process of electron transport and signal introduction. A model that includes charge transport would include bending in the electric field lines and variations in rise times and arrival times. The example simulations also do not model gaps between pixels or anti-scatter grid. Depending on the pulse shaping time, photons that arrive near the boundary of two pixels may experience incomplete collection or arrive at different times at the two pixels.

In the examples and simulations described herein, the time-dependent signal was modeled in a block of PCD pixels. In most of the simulations, the block of detector modeled was 60 by 20 pixels. The time discretization in the simulations was 10 ns. As x-ray photons arrive on the PCD surface, they are rounded in the nearest 5 keV interval, the nearest 10 ns time discretization interval, and the changes in a local 5 by 5 neighborhood of pixels is increased following a random entry in the precomputed table. The energies in these pixels is convolved with a unipolar Gaussian pulse response function. Up-crossings of a comparator threshold boundary are then counted and stored in an energy bin counter. In this example, if an up-crossing in the LLD coincides with an up-crossing in the LLD of the right or down (also call east or south) pixels with an 80 ns time window (See Table 2), the CCB is incremented. The incident X-ray spectrum may be estimated using known tools for x-ray spectral analysis and in this example was estimated as 120 kVp. The flux was tuned so that in the absence of any background object, the arriving flux would be $1.0*10^9$ photons per mm² per s. This is very roughly the maximum output of diagnostic CT x-ray tubes today at 120 kVp. The passage of these X-ray photons through the object was calculated with Poisson statistics, neglecting scatter originating within the object.

All simulations were performed in projection mode only, not in CT reconstruction. Over one readout, the output of the simulations was the detector bin data across a block of PCD pixels. In the examples and simulations described herein, five energy bins were used from 25 to 105 keV at 20 keV intervals. These thresholds were not optimized. However, in some simulations, only the 25 and 65 keV bins were processed, in order to emulate the functionality of a 2-bin detector.

As mentioned above, an estimator (e.g., estimator 140 shown in FIG. 1) may be used to convert raw bin data into spectral images. The raw bin data for a PCD pixel may described by a vector b, with component elements $b_k$ corresponding to integers that record the number of counts detected in that bin. A two basis material decomposition may be used consisting of iodine and water. The estimator tasks that are considered in the examples and simulations are the creation of iodine basis material images, water basis material images, iodine contrast-noise ratio (CNR) images, and water CNR images.

In an embodiment, the estimator is a noise-efficient, computationally fast and artifact-free estimator in the presence of various PCD non-idealities. In the examples and simulations described herein, a first-order linear expansion of the optimal estimator is used that is of the form $$f(b) \cong c_0 + \sum_{k=1}^{N_{bins}} c_k b_k \quad \text{Eqn. (1)}$$

where $c_k$ are constant multipliers that are chosen for the specific task, and correspond to the first order expansion of the true estimator about a specific operating point. $N_{bins}$ corresponds to the number of bins, which is up to 6, comprising 5 energy bins and 1 CCB.

To solve for $c_k$, a phantom was used that included a background object which was a uniform layer of water. Two low contrast objects were placed on top of the background object. One low contrast object was composed of water, and the other was iodine. Different values of $c_k$ may be created for each choice of pixel pitch, background object thickness, and x-ray tube output. The thickness of both objects was chosen so that they reduced transmitted flux by 20%. These low contrast objects were 11×11 pixels in size. Three 11×11 regions of interest (ROIs) were defined, and the bin data in each ROI was averaged together to produce three vectors. The simulation was repeated $N_{sim}$=3000 times to collect statistics. The results of these simulations were three matrices, $bkgd_{ik}$, $iodine_{ik}$, and $water_{ik}$, with each matrix of size $N_{sim} \times N_{bins}$. These matrices were then averaged in the simulation index direction to produce three averages, $\overline{bkgd_k}$, $\overline{iodine_k}$, and $\overline{water_k}$. For the iodine material decomposition task, $c_k$ was then optimized according to the problem:

$$\text{minimize } \Sigma_i (\Sigma_k \, bkgd_{ik} c_k)^2 \quad \text{Eq. (2)}$$

$$\text{subject to } \Sigma_k \overline{iodine_k} c_k = 1 \quad \text{Eq. (3)}$$

-continued $$\Sigma_k \overline{bkgd_k} c_k = 0 \quad \text{Eq. (4)}$$

$$\Sigma_k \overline{water_k} c_k = 0 \quad \text{Eq. (5)}$$

The three constraints, Equations (3-5), enforce that the estimator is unbiased. Averaged over all simulations, the background and water areas must not contain iodine, and the iodine ROI must contain a fixed amount of iodine. Among all possible linear estimators that meet the criteria of being unbiased, the objective function, Equation (2), selects the estimator with minimum variance in the background region. It should be noted that this is not variance within an ROI, which changes according to system resolution and decreases when a blurring filter is applied. Rather, the quantity in Equation (2) has already been averaged in the ROI and is only minimally affected by variation in resolution.

All other estimators are obtained in a similar fashion. To obtain $c_k$ for PCDs without the CCB, an additional constraint was included to restrict its corresponding value of $c_k$ to 0. To obtain $c_k$ for PCDs with 2 instead of 5 energy bins, the $c_k$ for energy bins 2, 4, and 5 were zero, leaving only the first and third energy bin at 25 and 65 keV. To obtain $c_k$ for the iodine CNR task, the constraint in Equation (5) was eliminated, so that the water material no longer is canceled. To obtain $c_k$ for water basis material decomposition, the right hand sides in Equation (3) and Equation (5) were switched.

Figure 3:
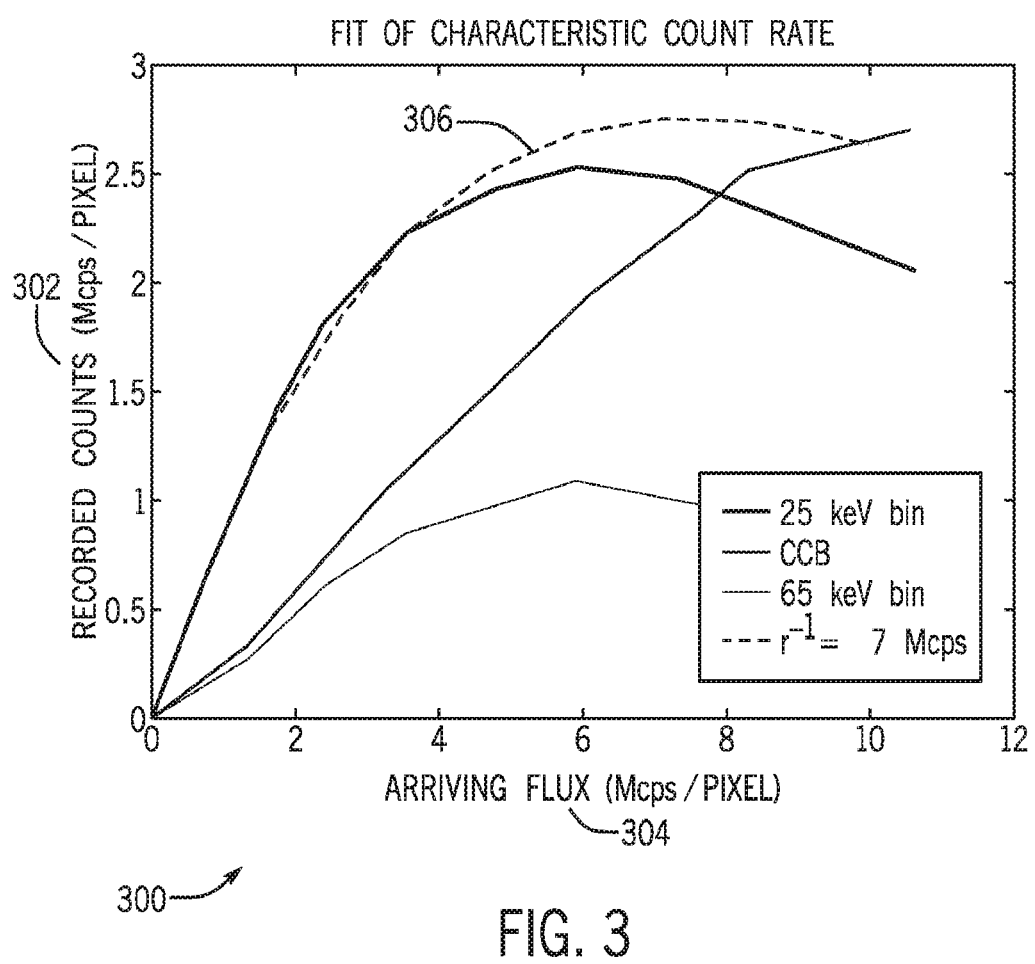
FIG. 3 shows a graph of an example of a simulated recorded count rate as a function of incident count rate that was used to derive a characteristic count rate in accordance with an embodiment.

Table 2 shows the basic parameters of the example system for simulations. FIG. 3 shows a graph 300 of an example of a simulated recorded count rate 302 as a function of incident count rate 304 that was used to derive a characteristic count rate. Some points in FIG. 3 correspond to very high unattenuated incident flux (~$10^{10}$ counts/mm²-s) that may not be physically achievable, because 20 cm of water filtration was used to get a spectrum representative of later experiments. Reasonable agreement was found with a paralyzable detector with characteristic count rate of 7 Mcps/pixel, but divergence is seen at high count rates. In this examples, the characteristic count rate is an empirical fit to a paralyzable detector model. Incident spectrum was filtered by a 20 cm object and a 30 micron pixel pitch was used. The dashed line 306 in FIG. 3 is an ideal paralyzable detector. To estimate the error of the process, each set of 3,000 simulations was repeated 6 times to produce sample average and sample standard deviation values.

TABLE 2

| Parameter | Value |
| --- | --- |
| Tube spectrum | 120 kVp |
| Energy thresholds, 2 bin | 25, 65 keV |
| Energy thresholds, 5 bin | 25, 45, 65, 85, 105 keV |
| Pixel pitch | 200, 300, or 400 microns |
| Basis material selection | Iodine and water |
| Electronic noise | None modeled |
| Pulse shaping function | Gaussian, σ = 40 ns, FWHM = 94 ns |
| Characteristic count rate | 7 Mcps/pixel |
| Dead time | 143 ns |
| Coincidence detection timing | 40 ns, before or after |
| | 80 ns, total interval |
| Time discretization interval | 10 ns |
| Time duration | 20 microseconds, 0.2 mm pixel pitch |
| | 8.89 microseconds, 0.3 mm pixel pitch |
| | 5 microseconds, 0.4 mm pixel pitch |
| Simulation count ($N_{sim}$) | 3000 per set * 6 sets |

In an example, several non-idealities of the PCD detector were sequentially eliminated (or ablated) to better gain insight on the mechanism of the CCB. In so doing, the PCD with CCB was able to be compared to two other systems that lay in between the PCD with CCB and the ideal PCD: (1) a PCD ACS and (2) a PCD ACS LLD. The PCD ACS is a PCD with analog charge summing in a 5×5 neighborhood. This is an upper bound on the performance of any analog charge summing circuit implementation, which more typically sums in a 2×2 or 3×3 neighborhood. Compared to the ideal PCD, however, this system suffers from k-escape, long-range Compton scatter, and punch-through (high energy X-ray photons that do not interact with the CdTe substrate due to its finite length). These non-idealities cannot be salvaged by any kind of charge sharing compensation. Additionally, some implementations of analog charge summing are only triggered when digital coincidences are detected in neighboring pixels. This may further reduce performance. The implementation of PCD ACS in the examples described herein is always active. The PCD ACS LLD is a PCD with analog charge summing in a 5×5 neighborhood, but summing is performed only if the charge in a pixel exceeds the lowest level discriminator. This represents an upper bound on digital count summing anti-coincidence logic, which reconstructs charge based on the output digital of comparator threshold crossings. Any such circuit must necessarily disregard charge in a pixel that is below the LLD. In practice, the performance of anti-coincidence logic would be further reduced by the ambiguity within energy bins. With anti-coincidence logic, it may only be known that the charge in a pixel resides between two energy thresholds (e.g., somewhere between the 25 keV threshold and 45 keV threshold). The PCD ACS LLD system assumes that this information is known.

Both the PCD ACS system and the PCD ACS LLD system perform charge summing instantaneously and without any penalty to count rate capability, and were implemented with a delta pulse shape so that they are essentially immune to pileup. The PCD ACS and PCS ACS LLD are compared to the PCD with CCB at very low flux. The intent of the ablation analysis is to understand the information that is captured with the CCB compared to charge summing schemes, not to analyze their comparative performance at moderate or high flux conditions.

Figure 4:
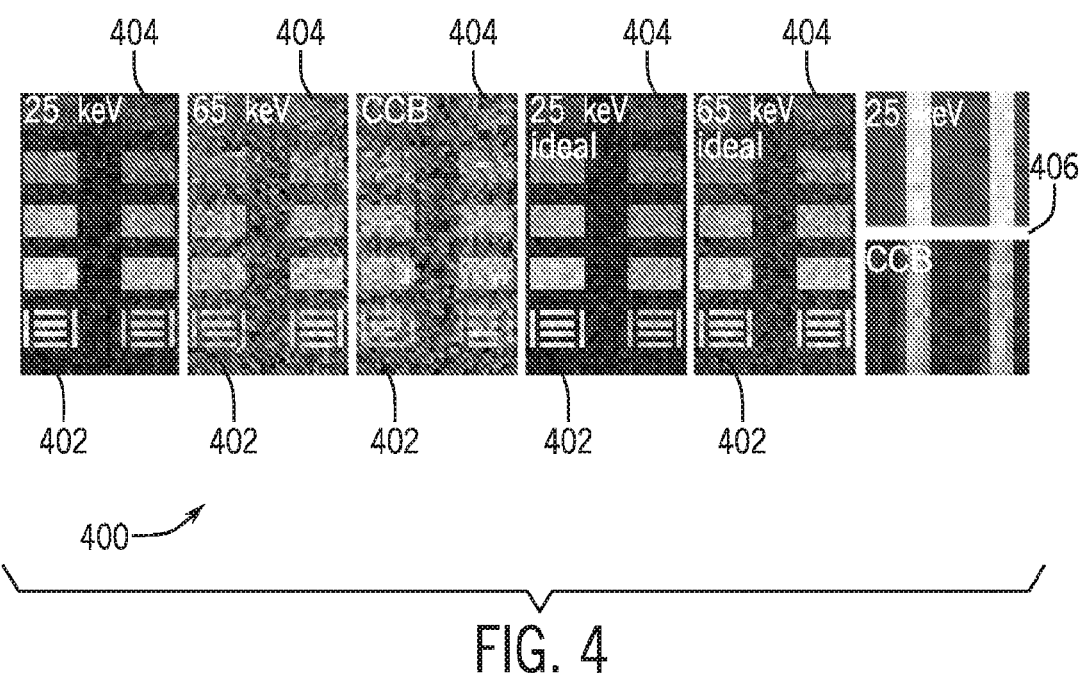
FIG. 4 shows example data from simulations of a low contrast phantom, with 1000 frames averaged to improve visibility in accordance with an embodiment.

FIG. 4 shows example data 400 from simulations of a low contrast phantom, with 1000 frames averaged to improve visibility. FIG. 4 shows raw bin data only of select thresholds (the left five subfigures). The left five subfigures include a column of iodine targets 402 on the left side and water targets 404 on the right side. It is noted that that this is raw bin data, not its logarithm, and hence increased attenuation appears dark. The different energy bins and the CCB present slightly different contrast from water and iodine, and when combined together appropriately, one of the materials can be canceled for the purpose of material decomposition. In FIG. 4, simulated data for an ideal detector is also included for comparison. FIG. 4 also shows a zoomed in subplots of a very high contrast line phantom 406. A binary mask is applied to the brightest target of each to create the line pair phantom 406. This was done to evaluate possible shift effects that may arise from the directional nature of the CCB, and also to quantitatively visualize possible changes in the modulation transfer function at high spatial frequencies. The lines, which are 3 pixels wide in the 25 keV image, show a faintly visible westward bias in the CCB image because of the directional nature of coincidence, which maps any horizontal coincidence detection to the left pixel. The low contrast targets are of different amplitude, and multiple frames of this object were averaged together to improve visibility.

Figure 5:
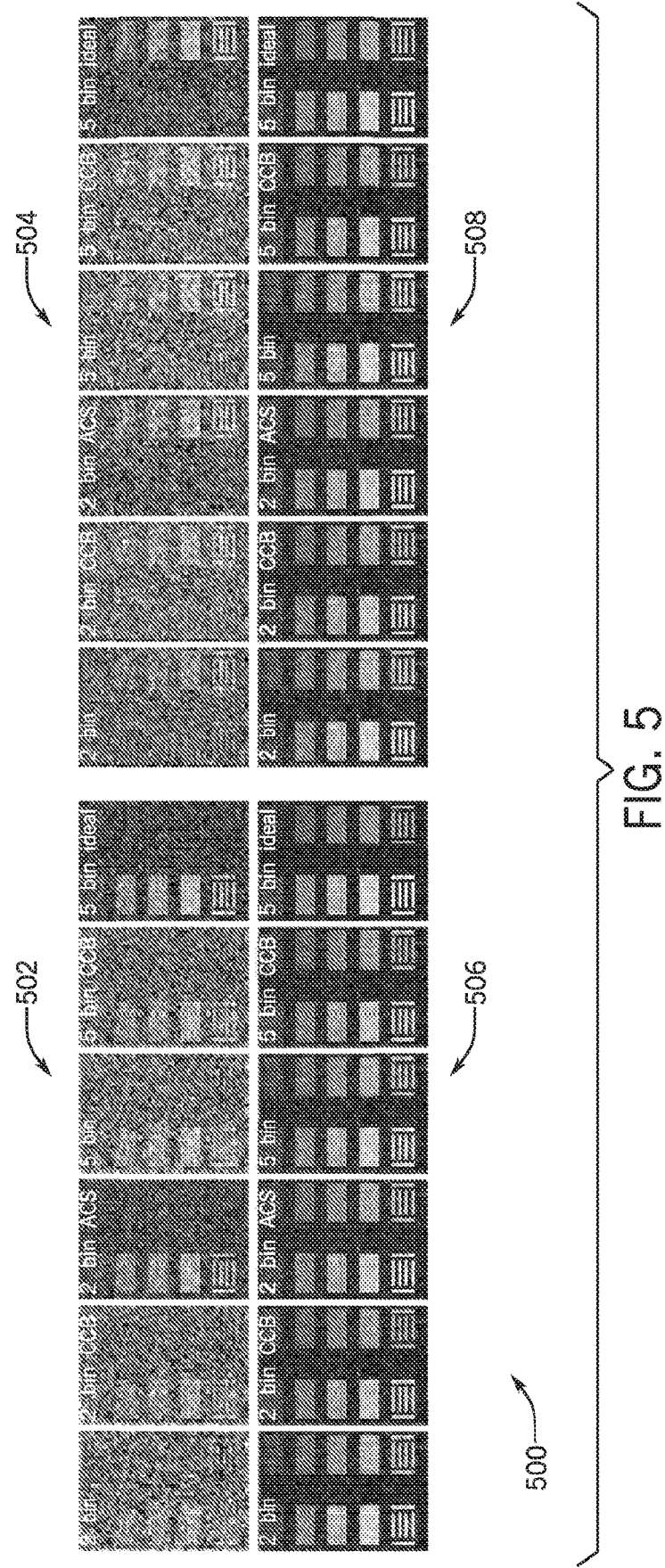
FIG. 5 shows example spectral images generated by an estimator and optimized for either material decomposition or CNR objectives in accordance with an embodiment.

The estimator derived from convex optimization (described above) is used to combine these bins in a linear fashion to generate spectral images optimized for either material decomposition or CNR objectives. FIG. 5 shows example spectral images generated by the estimator and optimized for either material decomposition or CNR objectives. All figures correspond to a 200 micron detector on a background thickness of 30 cm. The top left images 502 show iodine material decomposition and the top right images 504 show water material decomposition. The bottom left images 506 show optimization for iodine CNR and the bottom right images 508 show optimization for water CNR. The spectral images 500 in FIG. 5 show that the estimator described above is able to correctly cancel water or iodine in material decomposition tasks. In the water material decomposition images 504, the thickest iodine targets are barely visible, showing breakdown of the linear approximation in the spectral estimator. The CCB is able to subjectively improve the detectability of the targets in the material decomposition task. In the material decomposition, the source bins are combined to cancel the other basis material, so only one type of target appears visible. In FIG. 4, the linear pair phantom 406 appears poorly resolved with the raw CCB bin image. However, in FIG. 5, when the CCB bin is included in the estimator, it appears that the material decomposition is better resolved with the CCB. The blurring that is seen in the CCB images is anti-correlated with the bluffing that s introduced by charge sharing, so including the CCB into the estimator appears to improve visibility in this high frequency task.

To quantify this improvement, the signal in a rectangular ROI of an iodine insert is averaged and the averaged signal in a rectangular ROI of the same size in the background is subtracted to calculate the contrast in a single frame. This is calculated for each image in the set of 1000 noise realizations and then the contrast-to-noise-ratio-squared ($CNR^2$) can be calculated, where the noise is calculated over independent noise realizations rather than over spatial coordinates. In so doing, it was found that compared to the "2 bin" system, the (1) "2 bin CCB" system, (2)"5 bin" system, (3) "5 bin CCB" system, and (4) "5 bin ideal" system improve $CNR^2$ by 2.4×, 1.7×, 3.6×, and 12.6×, respectively. As described further below, the benefit of the CCB is numerically quantified in a simpler low-contrast phantom and its dependence on pixel size, flux, and object thickness is discussed.

Figure 6:
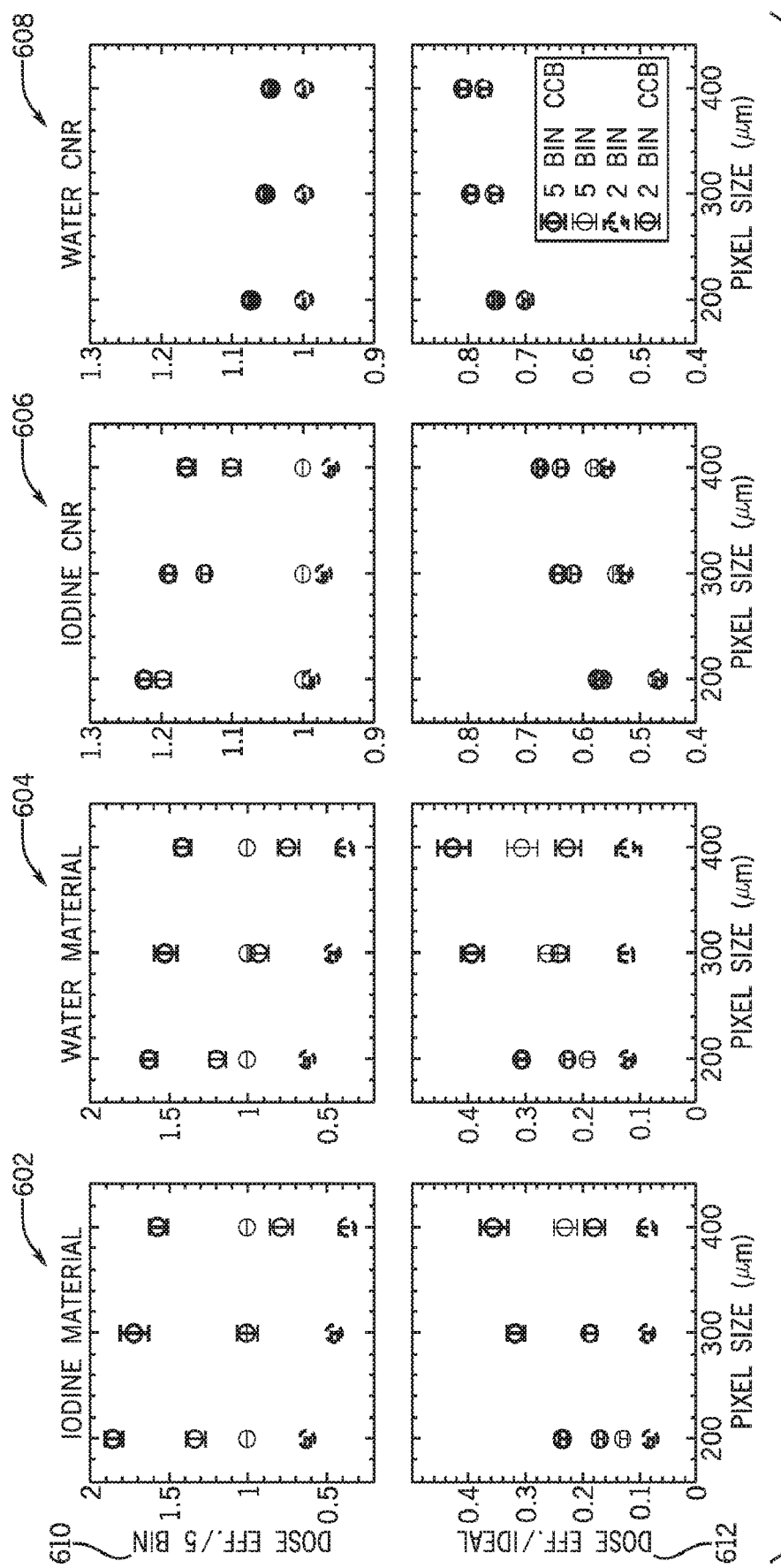
FIG. 6 shows graphs of an example quantification of the dose improvement factor in the low flux regime for each of the tasks (a) creation of iodine basis material images, (b) creation of water basis material images, (c) creation of iodine contrast-noise ratio (CNR) images, and (d) creation of water CNR images, as a function of pixel size n accordance with an embodiment.

FIG. 6 graphs of example quantification of the dose improvement factor in the low flux regime for each of the four tasks (creation of iodine basis material images 602, creation of water basis material images 604, creation of iodine contrast-noise ratio (CNR) images 606, and creation of water CNR images 608) as a function of pixel size. Specifically, FIG. 6 shows dose improvement factors for four detector architectures and three different pixel sizes. The values in FIG. 6 are derived from the variance in the background region of interest (ROI) average in the convex optimization process, which is then converted to an equivalent dose improvement. Dose improvement is inversely proportional to measured variance. In FIG. 6, the four columns 602, 604, 606, 608 correspond to different spectral tasks, including both basis material decomposition and optimal CNR. FIG. 6 also shows performance normalized to the 5 bin ideal PCD, which allows comparison between pixel sizes. In the top row 610, data are normalized to the 5-bin detector without CCB, which is therefore always plotted at unity. In the bottom row 612, data is normalized to the 5-bin ideal PCD, allowing comparison across pixel sizes. The ideal PCD is not affected by charge sharing, punch through, or k-escape. The simulation of the ideal PCD would be affected by pileup only if two photons arrive at the same 10 ns time discretization interval, a very rare event. The results in FIG. 6 are shown at low flux, with an object thickness of 30 cm of water. For the 200 micron pixel pitch, the flux of the unattenuated beam was 1000 Mcps/mm$^2$. The flux of the beam for 300 and 400 microns was reduced by 45% and 75%, respectively, so that the incident count rate on a per-pixel basis would be constant. In all cases, the incident count rate was 1.1% of the characteristic count rate. FIG. 6 also includes the relative dose efficiency for the 2-bin detector with and without the CCB for comparison. Overall, in this low flux scenario and assuming 5 energy bins, the dose efficiency in iodine material decomposition tasks was improved by 85% to 55% in the range between 200 microns to 400 microns. The improvements were less than 10% for water CNR and between 15% and 25% in iodine CNR.

Figure 7:
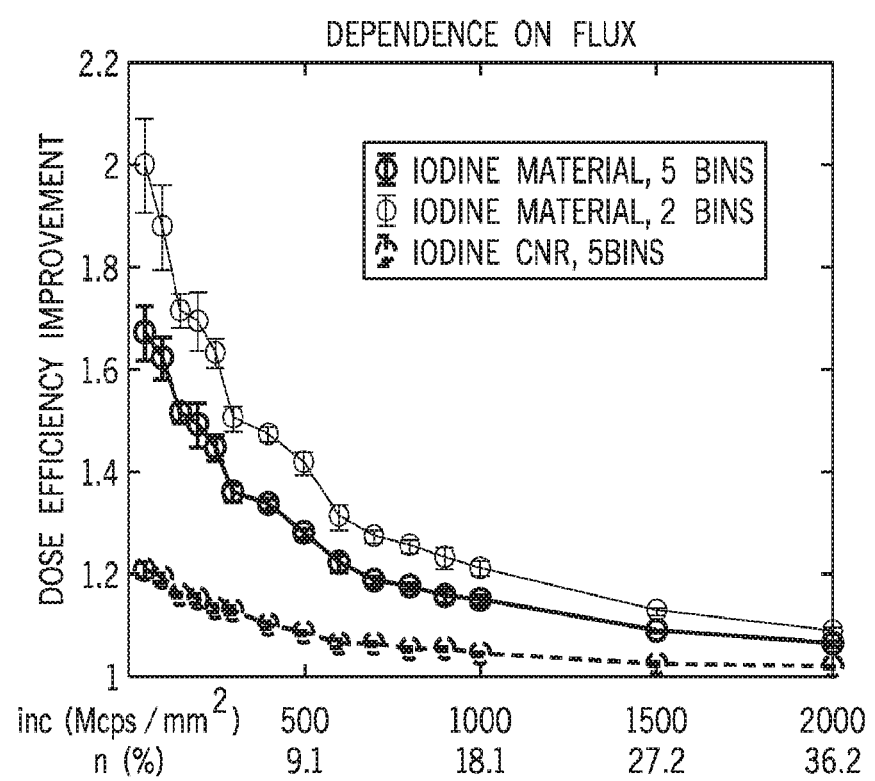
FIG. 7 shows a graph of an example improvement in dose efficiency for the material decomposition task as a function of incident flux for a 5-bin CCB PCD relative to a configuration without the CCB in accordance with an embodiment.

FIG. 7 shows a graph 700 of an example improvement in dose efficiency for the material decomposition task as a function of incident flux for the 5-bin CCB PCD relative to the configuration without the CCB. The pixel pitch was 300 microns and the background object thickness was 20 cm of water. The performance of the CCB rapidly decays with increasing flux, and many of its benefits are lost when the incident count rate is approximately 10% of the characteristic count rate. The highest flux value shown in this figure may not be attainable with current diagnostic X-ray tubes. However, higher incident count rates would certainly be achieved at thin object thicknesses. In FIG. 7, the x=axis "inc" corresponds to incident flux for the unattenuated beam in Mcps/mm$^2$. The second x-axis, $\eta$, converts this quantity to the arriving flux as a percentage of the characteristic count rate. Error bars show one standard deviation. It should be noted that the improvement factor for 2-bins with CCB is normalized to the 2 bin architecture without CCB, and the improvement factor for 5 bins with CCB is separately normalized to the 5 bin architecture without CCB.

Figure 8:
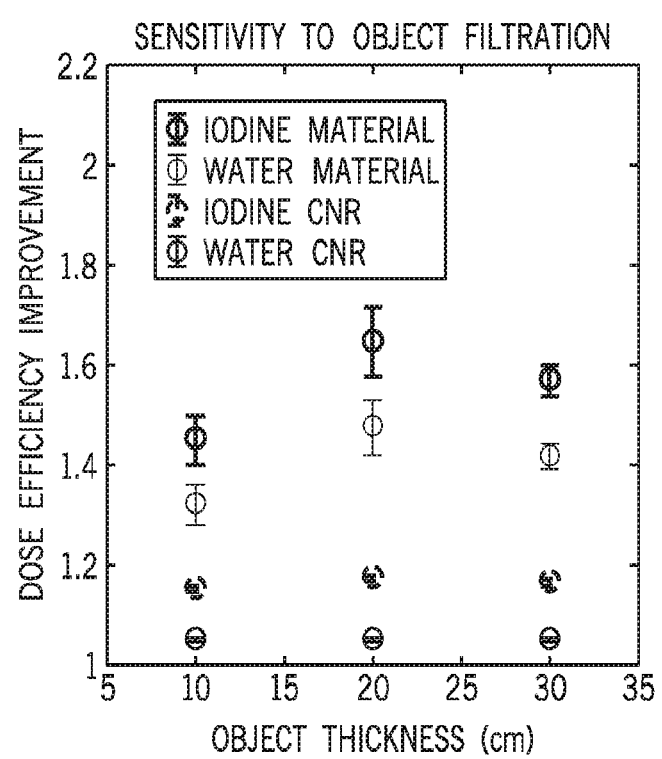
FIG. 8 shows a graph of an example performance of a CCB as a function of object thickness for the 300 micron pixel pitch detector in accordance with an embodiment.

FIG. 8 shows a graph 800 of an example the performance of the CCB as a function of object thickness for the 300 micron pixel pitch detector. The "object thickness" refers to the thickness of the background layer of water, not the thickness of the low contrast objects that are placed on top of the background to evaluate image quality. Accordingly, an object of water only is assumed. The flux transmitted through the object is constant and corresponds to approximately 2.5% of the characteristic count rate, which corresponds to an unattenuated incident flux of 1000 Mcps/mm$^2$ at 30 cm of object thickness. At reduced object thickness, the incident flux (simulated tube mA) was reduced to keep the flux arriving at the detector constant. The purpose of this experiment was primarily to examine sensitivity of the CCB to variations in the spectrum which are caused by additional object filtration. It was found that these variations are minor, and that the improvement is on the order of 50% to 60% between 10 and 30 cm of water. The improvements here are less than those seen in FIG. 6 because of the increase in flux from 1.1% to 2.5% of the characteristic count rate, which further illustrates that the benefits of the CCB rapidly disappear with increasing flux.

Figure 9:
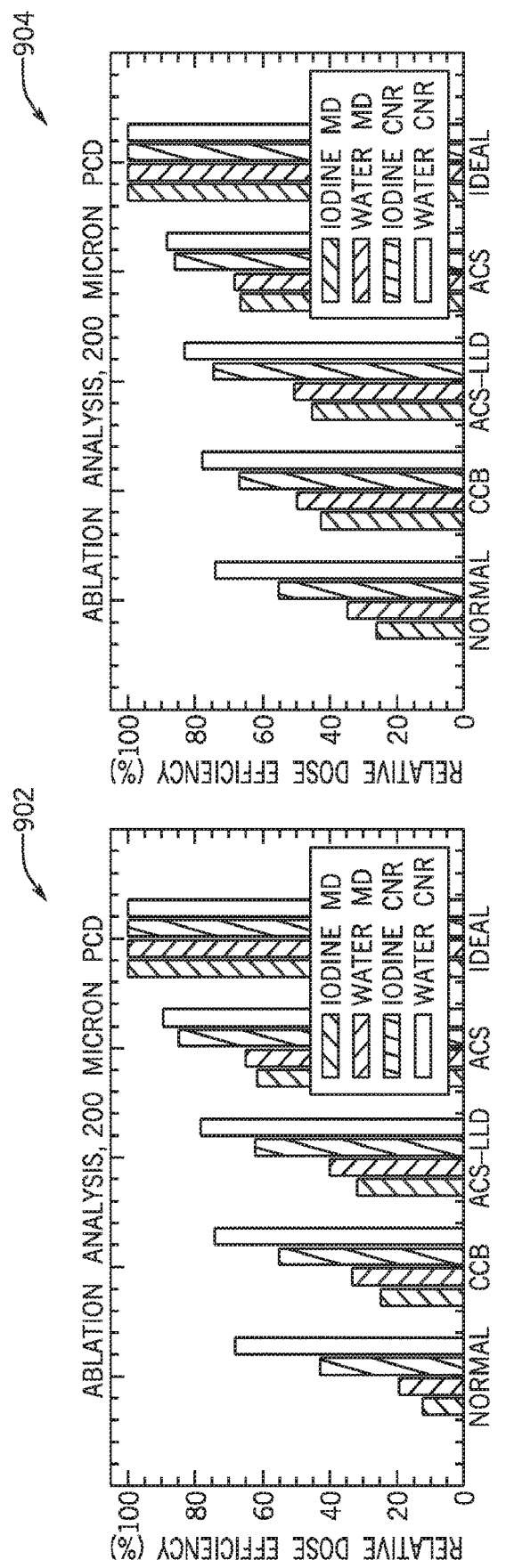
FIG. 9 shows graphs of an example result of an ablation analysis, normalized to the dose efficiency of an ideal system in accordance with an embodiment.

FIG. 9 shows graphs of an example result of an ablation analysis, normalized to the dose efficiency of an ideal system. These simulations were performed with 20 cm of water background thickness so that the flux was very low throughout. With the 200 micron detector, the unattenuated incident flux was 50 Mcps/mm$^2$ incident flux, and for the 400 micron detector, it was 12.5 Mcps/mm$^2$. The incident count rate was less than 1% of the characteristic count rate in all cases. As described above, the two systems that lay in between the PCD with CCB and the ideal PCD, ACS and ACS-LLD, provide an upper bound on the performance of analog charge summing (ACS) and digital count summing (DCS), respectively. In addition, FIG. 9 shows relative dose efficiency of detector systems that are increasingly more ideal, for both 200 micron 902 and 400 micron 904 pixel size. In FIG. 9, ACS is analog charge summing, and ACS LLD is analog charge summing above the lowest level discriminator (25 keV). All PCDs have 5 energy bins. "MD" is the material decomposition task. Error bars are not overlaid, but standard deviation for all bars is less than 4%.

For the 200 micron 902 detector, the CCB improves iodine material decomposition by about 100%. The additional benefit (above CCB) available to DCS is 30%, whereas for ideal ACS, it is 150%. At low flux, charge summing circuits outperform the CCB. The CCB does not directly restore photon observations on an event-by-event basis as the charge summing circuits do. However, it is surprising to see that the CCB extracts most of the information that is available after comparator digitization, as bounded by the ACS-LLD system. Substantially more information is available below the LLD for the simple reasons that charge sharing into an adjacent pixel is often insufficient to trigger the LLD.

The analysis of the 400 micron 904 detector is similar, except that all benefits are reduced because there is less charge sharing to correct. Compared to the non-CCB detector, the CCB improves iodine material decomposition by about 65%. DCS and ACS provide an additional 5% and 60%, respectively. Finally, it should be pointed out that the truly ideal PCD performs substantially better that ACS because it does not include models of long range Compton scatter, and punch-through. While punch-through might be eliminated with thick detectors, k-escape and long-range Compton scatter will probably never be corrected.

As mentioned above, in an embodiment the CCB can be realized by simply replacing a comparator with digital coincidence logic, which converts a regular energy bin into the CCB. Charge summing is more complex than CCB, which requires only digital communications and coincidence logic between neighboring pixels. The improvements from the CCB can be large, and FIG. 6 shows that, for the case with 5 energy bins and low flux, the CCB enables a 200 micron detector to perform as well as a detector twice its size. This suggests that the CCB would perform at least as well as flex circuits or parallel signal processing that bin together signals of 2×2 pixel blocks. Furthermore, the CCB would degrade gracefully with increasing flux.

It is surprising that the CCB is able to combat charge sharing because it does not actively identify and reconstruct instances of charge sharing. The ablation analysis in FIG. 9 shows that, in fact, the CCB captures most of the available information after comparator digitization. One explanation that is relevant for iodine CNR tasks is as follows. PCDs are expected to outperform energy-integrating detectors because energy-integrating detectors provide decreased weighting to low-energy, signal-rich photons. On the other hand, in the presence of charge sharing, PCDs often confuse high energy photons as two low energy photons, reducing the statistical value of low energy detection. At the low flux limit, each count in the CCB indicates that a low energy photon has been overcounted. Correcting this overcounting improves the statistics of the measurement.

The value provided by the CCB shows moderate variation in the range between 200 and 400 micron pixel pitch, with smaller pixel sizes presenting more charge sharing and hence greater benefits from charge sharing compensation. The dependence on object thickness, at equal flux incident on the detector, was modest. However, the dependence on flux was very strong. The benefits of the CCB shrink considerably above 10% of the characteristic count rate. However, it should be pointed out that the regions in the sinogram with the lowest flux are also the regions where noise reduction is the most important.

As discussed above, the present disclosure describes coincidence counting for charge sharing compensation, specifically, each charge sharing event is counted rather than attempting an event-by-event correction. As mentioned, surprisingly, coincidence counting captures most of the information content available after comparator digitization. Because of its similarities to existing energy bins, the CCB is simple to implement. Because it improves material decomposition dose efficiency by 50-100% at low flux and does not damage count rate capability at high flux, it may be attractive for spectral CT, where both spectroscopic accuracy and count rate are important. In an embodiment, PCDs with more than two energy bins and no other charge sharing compensation may benefit from converting an existing energy bin into a coincidence counter.

Figure 10:
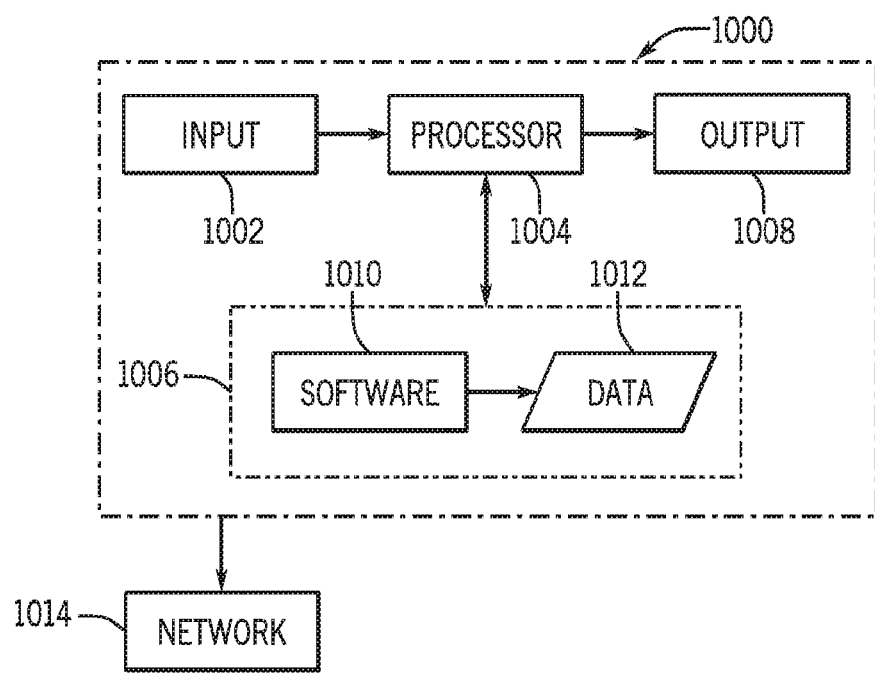
FIG. 10 is a block diagram of an example computer system in accordance with an embodiment.

FIG. 10 is a block diagram of an example computer system in accordance with an embodiment. Computer system 1000 may be used to implement various methods described herein. The computer system 1000 generally includes an input 1002, at least one hardware processor 1004, a memory 1006, and an output 1008. Thus, the computer system 1000 is generally implemented with a hardware processor 1004 and a memory 1006. In some embodiments, the computer system 1000 may be a workstation, a notebook computer, a tablet device, a mobile device, a multimedia device, a network server, a mainframe, one or more controller, one or more microcontrollers, or any other general-purpose or application-specific computing device. In an embodiment, the computer system 1000 may be implemented in or coupled to a computer tomography (CT) imaging system.

The computer system 1000 may operate autonomously or semi-autonomously, or may read executable software instructions from memory 1006 or a computer-readable medium (e.g., hard drive a CD-RIOM, flash memory), or may receive instructions via the input from a user, or any other source logically connected to a computer or device, such as another networked computer or server. Thus, in some embodiments, the computer system 1000 can also include any suitable device for reading computer-readable storage media. In general, the computer system 1000 may be programmed or otherwise configured to implement the methods and algorithms described in the present disclosure.

The input 1002 may take any suitable shape or form, as desired, for operation of the computer system 1000, including the ability for selecting, entering, or otherwise specifying parameters consistent with performing tasks, processing data, or operating the computer system 1000. In some aspects, the input 1002 may be configured to receive data, such as imaging data, measurement data, and clinical data. In addition, the input 1002 may also be configured to receive any other data or information considered useful for implementing the methods described above. Among the processing tasks for operating the computer system 1000, the one or more hardware processors 1004 may also be configured to carry out any number of post-processing steps on data received by way of the input 1002.

The memory 1006 may contain software 1010 and data 1012, such as imaging data, clinical data and molecular data, and may be configured for storage and retrieval of processed information, instructions, and data to be processed by the one or more hardware processors 1004. In some aspects, the software 1010 may contain instructions directed to implementing one or more machine learning algorithms with a hardware processor 1004 and memory 1006. In addition, the output 1008 may take any form, as desired, and may be configured for displaying images, patient information, parameter maps, and reports, in addition to other desired information. Computer system 1000 may also be coupled to a network 1014 using a communication link 1016. The communication link 1016 may be a wireless connection, cable connection, or any other means capable of allowing communication to occur between computer system 1000 and network 1014.

Computer-executable instructions for charge sharing compensation for x-ray photon counting detectors according to the above-described methods may be stored on a form of computer readable media. Computer readable media includes volatile and nonvolatile, removable, and non-removable media implemented in any method or technology for storage of information such as computer readable instructions, data structures, program modules or other data. Computer readable media includes, but is not limited to, random access memory (RAM), read-only memory (ROM), electrically erasable programmable ROM (EEPROM), flash memory or other memory technology, compact disk ROM (CD-ROM), digital volatile disks (DVD) or other optical storage, magnetic cassettes, magnetic tape, magnetic disk storage or other magnetic storage devices, or any other medium which can be used to store the desired instructions and which may be accessed by a system (e.g., a computer), including by internet or other computer network form of access.

The present invention has been described in terms of one or more preferred embodiments, and it should be appreciated that many equivalents, alternatives, variations, and modifications, aside from those expressly stated, are possible and within the scope of the invention.

The invention claimed is:

1. A system for charge sharing compensation for a photon counting detector comprising:
    a plurality of comparators, each of the plurality of comparators configured to generate comparator output data based on a threshold value;
    a plurality of energy bins, each of the plurality of energy bins coupled to one of the plurality of comparators;
    a coincidence logic coupled to two or more of the plurality of comparators and configured to receive comparator output data associated with two or more of a plurality of pixels, the comparator output data for each pixel indicating when a signal associated with the pixel crosses a threshold value, the coincidence logic configured to generate a coincidence output when the comparator output data for a first pixel is received within a predetermined time interval of the comparator output data for a second pixel; and
    a coincidence counting bin coupled to the coincidence logic and configured to receive the coincidence output and generate count data indicating a number of detected coincidences between pixels based on the coincidence output.

2. The system according to claim 1, further comprising an estimator coupled to the coincidence counting bin and the plurality of energy bins and configured to generate an image based on the count data from the coincidence counting bin and data from each of the plurality of energy bins.

3. The system according to claim 2, further comprising a display coupled to the estimator and configured to display the image.

4. The system according to claim 1, wherein the plurality of pixels is a plurality of adjacent pixels.

5. The system according to claim 1, wherein the first pixel and the second pixel are adjacent pixels.

6. The system according to claim 1, wherein the comparator output data is lowest level discriminator data.

7. The system according to claim 1, wherein the count data is incremented in response to receipt of the coincidence output.

8. The system according to claim 2, wherein the estimator generates a spectral image.

9. A method for charge sharing compensation for a photon counting detector comprising:
providing comparator output data associated with each of a plurality of pixels from a plurality of comparators to a coincidence logic and a plurality of energy bins, the comparator output data for each pixel indicating when a signal associated with the pixel crosses a threshold value;
generating, using the coincidence logic, a coincidence output when the comparator output data for a first pixel is received within a predetermined time interval of the comparator output data for a second pixel;
generating count data indicating a number of detected coincidences between pixels based on the coincidence output using a coincidence counting bin;
generating an image based on the count data and data from each of a plurality of energy bins; and
displaying the image.

10. The method according to claim 9, wherein the plurality of pixels is a plurality of adjacent pixels.

11. The method according to claim 9, wherein the first pixel and the second pixel are adjacent pixels.

12. The method according to claim 9, wherein the comparator output data is lowest level discriminator data.

13. The method according to claim 9, wherein the count data is incremented in response to receipt of the coincidence output.

14. The method according to claim 9, wherein the image is a spectral image.

* * * * *

UNITED STATES PATENT AND TRADEMARK OFFICE
CERTIFICATE OF CORRECTION

| | |
|---|---|
| PATENT NO. | : 12,000,970 B2 |
| APPLICATION NO. | : 17/602962 |
| DATED | : June 4, 2024 |
| INVENTOR(S) | : Scott S. Hsieh |

It is certified that error appears in the above-identified patent and that said Letters Patent is hereby corrected as shown below:

In the Specification

Column 12, Line 31, "bluffing" should be --blurring--.

Signed and Sealed this
Twentieth Day of August, 2024

Katherine Kelly Vidal
*Director of the United States Patent and Trademark Office*